US010267443B2

(12) United States Patent
Blake et al.

(10) Patent No.: US 10,267,443 B2
(45) Date of Patent: Apr. 23, 2019

(54) ASEXUAL FLUID CONNECTOR HAVING A CLAMP AND PROTECTION

(71) Applicant: SARTORIUS STEDIM FMT SAS, Aubagne (FR)

(72) Inventors: Florian Blake, Hyeres (FR); Jeremy Gibelin, Le Beausset (FR)

(73) Assignee: SARTORIUS STEDIM FMT SAS, Aubagne (FR)

( * ) Notice: Subject to any disclaimer, the term of this patent is extended or adjusted under 35 U.S.C. 154(b) by 398 days.

(21) Appl. No.: 14/392,172

(22) PCT Filed: Jun. 25, 2014

(86) PCT No.: PCT/FR2014/051608
§ 371 (c)(1),
(2) Date: Dec. 23, 2015

(87) PCT Pub. No.: WO2014/207385
PCT Pub. Date: Dec. 31, 2014

(65) Prior Publication Data
US 2016/0186906 A1     Jun. 30, 2016

(30) Foreign Application Priority Data
Jun. 28, 2013  (FR) ..................... 13 56353

(51) Int. Cl.
*F16L 37/098*     (2006.01)
*A61M 39/10*     (2006.01)
(Continued)

(52) U.S. Cl.
CPC ........ *F16L 37/098* (2013.01); *A61M 39/1011* (2013.01); *A61M 39/165* (2013.01);
(Continued)

(58) Field of Classification Search
CPC ... F16L 37/098; F16L 33/025; F16L 2201/10; F16L 2201/44; F16L 29/005;
(Continued)

(56) References Cited

U.S. PATENT DOCUMENTS 5,111,555 A * 5/1992 Oetiker ................. F16L 33/025
24/20 CW
2003/0030272 A1    2/2003 Johnson et al.
(Continued)

FOREIGN PATENT DOCUMENTS

EP     1281909 A2 *   6/2013   ....... F02M 35/10137
JP     2004232830 A *  8/2004   .......... F16L 37/0987

OTHER PUBLICATIONS

International Search Report issued in Application No. PCT/FR2014/051608, dated Jan. 20, 2015.

*Primary Examiner* — David Bochna
*Assistant Examiner* — James A Linford
(74) *Attorney, Agent, or Firm* — Young & Thompson

(57) ABSTRACT

Fluid-connection device for connecting a flexible pipe defining a first fluid space to a second flexible pipe or a flexible fluid enclosure in a biopharmaceutical assembly, includes a first connector and a second connector equivalent thereto, the first connector and second connector adapted to be coupled together in a genderless manner, by an insertion movement that is essentially an axial translation, into a relative coupling position, which defines a mating plane, each of the connectors including, in an alternating manner along the circumferential direction, N flexible snap-fitting tabs and N stop surfaces, the flexible snap-fitting tabs projecting axially forwards relative to the mating plane, and the stop surfaces being set back from the mating plane so that, in the coupling position, the snap-fitting tabs of one connector clip into place on the stop surfaces of the other (Continued)

connector, such that the resulting position is locked by the snap-fitting tabs.

13 Claims, 5 Drawing Sheets

(51) Int. Cl.
*A61M 39/18* (2006.01)
*F16L 33/025* (2006.01)
*A61M 39/16* (2006.01)
*A61J 1/14* (2006.01)

(52) U.S. Cl.
CPC .......... *A61M 39/18* (2013.01); *F16L 33/025* (2013.01); *A61J 1/1481* (2015.05); *A61M 2039/1027* (2013.01); *A61M 2039/1066* (2013.01); *A61M 2205/6072* (2013.01); *A61M 2205/6081* (2013.01); *F16L 2201/10* (2013.01); *F16L 2201/44* (2013.01)

(58) Field of Classification Search
CPC ............ A61M 39/165; A61M 39/1011; A61M 39/18; A61M 2205/6081; A61M 2205/6072; A61M 2039/1027; A61M 2039/1066; A61J 1/1481
See application file for complete search history.

(56) References Cited

U.S. PATENT DOCUMENTS

| | | |
|---|---|---|
| 2006/0192165 A1 | 8/2006 | Matkovich et al. |
| 2007/0001453 A1 | 1/2007 | Miyajima et al. |
| 2009/0208277 A1 | 8/2009 | Werth |
| 2010/0133807 A1 | 6/2010 | Bilstad et al. |
| 2010/0230950 A1 | 9/2010 | Williams et al. |
| 2012/0227221 A1 | 9/2012 | Whitaker et al. |

* cited by examiner

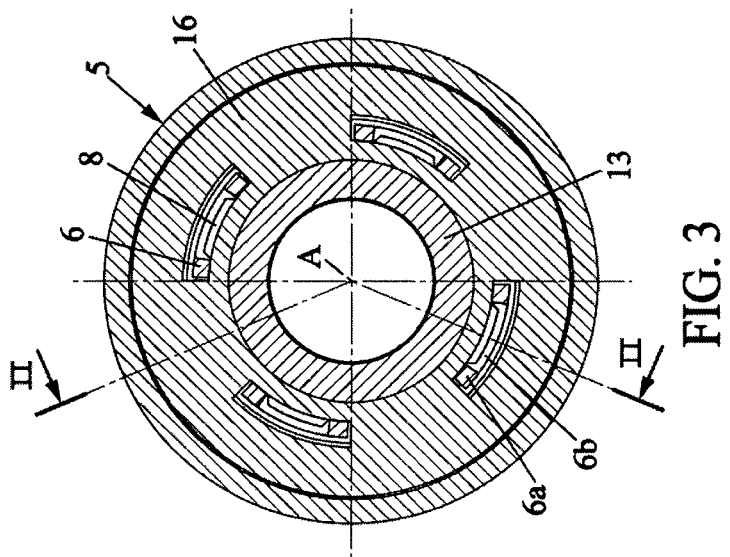
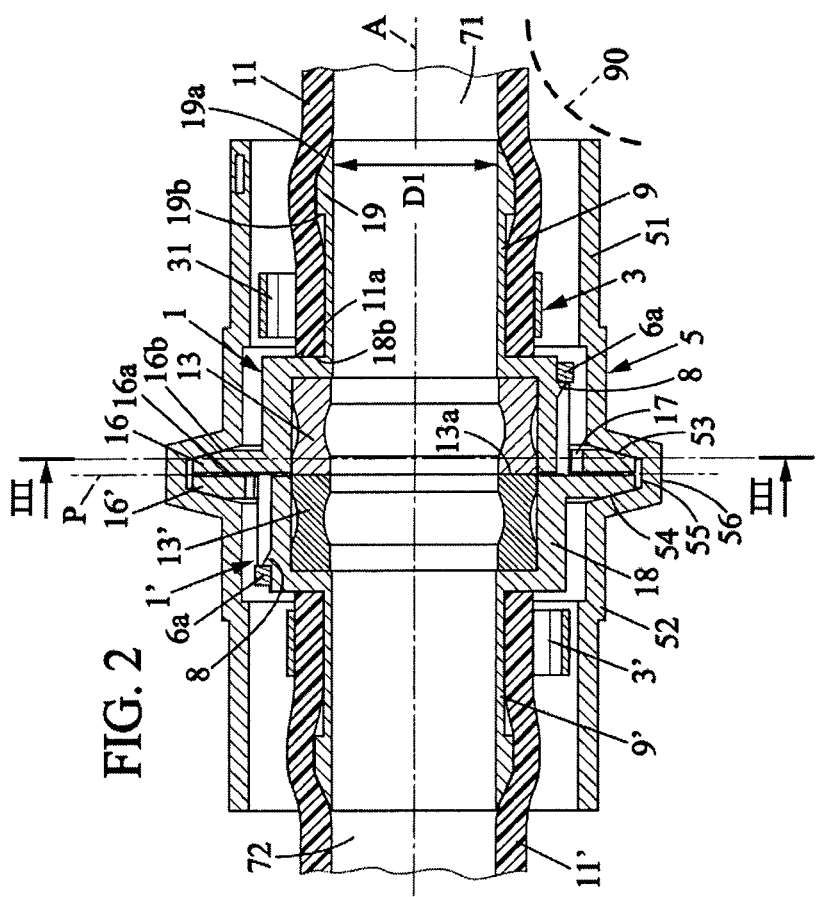

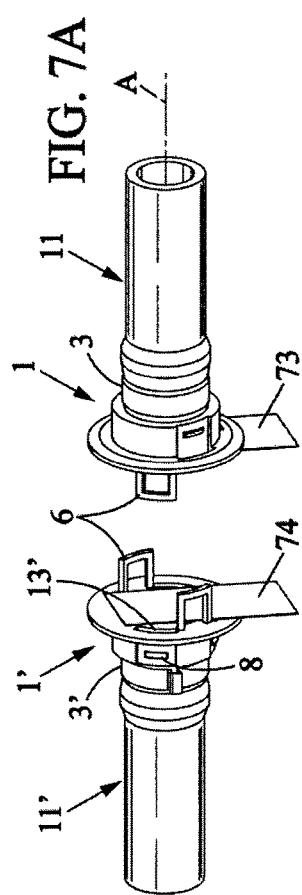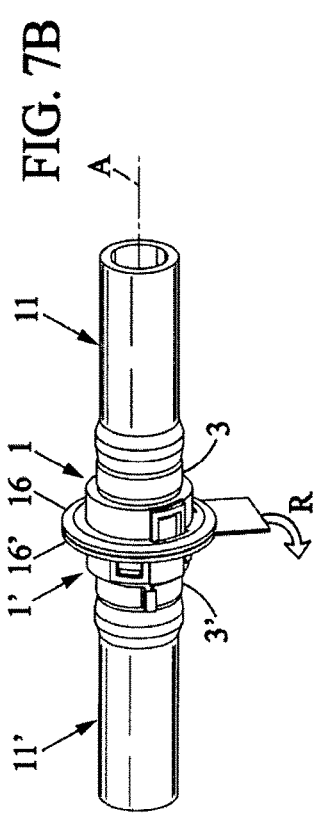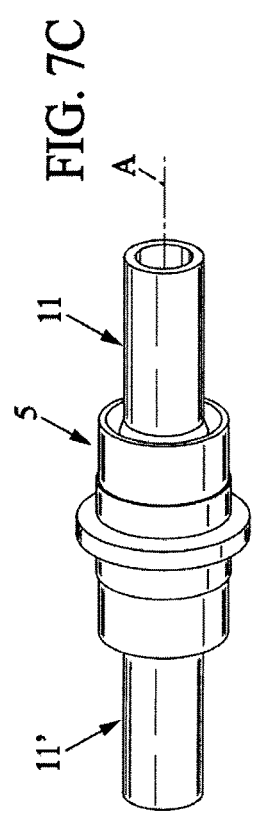

ASEXUAL FLUID CONNECTOR HAVING A CLAMP AND PROTECTION

FIELD OF THE INVENTION

The invention relates to fluid connections, in particular the fluid connection devices for connecting a fluid pipe to another pipe or to a container, in the field of biopharmaceutical applications.

BACKGROUND OF THE INVENTION

Specifically, the tubes or pipes used in the biopharmaceutical field are flexible or highly flexible pipes which are used to convey various biopharmaceutical substances, most often with the necessary aseptic precautions.

Fluid connection devices commonly comprise a first male connector (in other words forming a male interface) able to be received in a second complementary connector forming a female interface, which is a simple and well-understood solution. However, a male connector cannot be connected to another male connector, nor can a female connector be connected to another female connector.

In the context of assembling a flexible pipe to another pipe or container by means of a fluid connection, there is a need to improve the interoperability of the connectors in order to facilitate the construction of modular biopharmaceutical assemblies.

There are known fluidic connections for connecting together two "genderless" connectors that are functionally equivalent in terms of coupling. However, the known genderless fluid connectors generally require an axial insertion movement followed by a rotational movement about the axis.

In addition, the sterile or aseptic precautions for such applications necessitate good verification of the fluid connections established between the various entities in a biopharmaceutical assembly such as pipes, bags, filters, etc.

We therefore seek ways to check the coupling position in a simple and reliable manner, meaning to verify that the coupling movement has reached the correct final position, possibly being secured in this position by locking means.

For genderless connectors with axial translational movement followed by rotation, proper completion of the rotation is difficult to verify.

There is therefore a first need to provide a connection device for connecting together two genderless connectors with a coupling movement that only involves axial translational movement.

In biopharmaceutical applications, the flexible pipes allow the circulation, passage, and communication of a fluid, such as a biopharmaceutical fluid, and can either be connected to a similar flexible pipe or to a vessel or container which may be rigid or flexible.

The vessel or container in question may, in the current case, be a container for storing and/or processing content such as a biopharmaceutical product. In the current case, such a container is understood to mean a rigid or semi-rigid reusable container or a flexible disposable container such as a bag or even a filter cartridge.

This bag may be one of the substantially thin "2D" bags, such as those marketed by Sartorius Stedim Biotech under the brand Flexboy®, having a typical volume of between 50 ml and 50 liters. This flexible bag may also be a "3D" bag, such as those marketed by Sartorius Stedim Biotech under the brand Flexel®, having a larger volume and a substantial size in all three dimensions. Note that a pipe such as the pipe to which the invention applies can be placed between two bags or a larger number of bags.

A pipe such as that to which the invention is applied, usually of circular cross-section, is typically made of a plastic such as silicone, thermoplastic elastomers (TPE), or PVC, this list being non-limiting. It has a certain general stability and simultaneously both a certain overall flexibility and a certain local flexibility, allowing, when sufficient force is applied, crimping the pipe or substantially deforming it radially.

In a typical embodiment, for example, the pipe has an outer diameter between 8 mm and 30 mm for example, with the thickness depending on the material, the diameter, and the applications.

In the prior art, to couple such a flexible pipe, it is slipped over a tubular nozzle, whereupon a pipe clamp is placed around the pipe and then the clamp is tightened. The tightened clamp thus exerts a radial inward pressure to maintain the hose on the nozzle, on the one hand to ensure a good seal against the nozzle and on the other hand to prevent the pipe from detaching from the nozzle when pulled.

For such pipe clamps, a plastic clamp can be used for example, of polyamide for example such as Rilsan®. This type of plastic clamp, also sometimes called Serflex®, comprises a system of notches on a strip cooperating with a locking hook arranged in the head, such that the tightening is irreversible. In other words, once the strip is engaged in the head to form a loop, the strip is pulled to reduce the diameter of the loop and tighten the clamp; all return movement is prevented by the engagement of the hook in one of the strip notches. After tightening, to prevent the strip from projecting too far beyond the diameter of the clamp loop, the free portion of the strip is cut off near the head of the clamp. The undetached remaining portion of the strip often has a sharp edge which can cut.

As an alternative to the plastic clamp, a metal clamp can be used which is in the form of a preformed ring having one or two "ears" projecting outward with respect to the general shape of the ring of the clamp, this type of clamp sometimes being called an Oetiker® clamp. After insertion of the clamp onto the pipe to be retained, a tool is used to crimp the ear (or ears) of the clamp which causes permanent deformation and thus a narrowing of the major diameter of the ring and as a result tightens the clamp on the pipe. This type of clamping with a metal ring is particularly robust and reliable. However, at the point where the ear was crimped by the tool, there may be a burr or roughness which forms a sharp edge that can be damaging.

Whether plastic or metal, once such clamps are installed in biopharmaceutical assemblies, these assemblies may need to be transported or moved and therefore there is a risk of damage by the damaging parts of these clamps to other elements of the biopharmaceutical assembly, particularly the flexible bags or flexible pipes, which can cause a leakage or loss of sterilization that is detrimental to the biopharmaceutical application.

In addition, these clamps are easy to access (and thus can be removed) and does not guarantee a satisfactory image or aesthetics.

There is therefore a second need to prevent the pipe clamp from posing a danger to the surrounding elements.

OBJECTS AND SUMMARY OF THE INVENTION

Below is provided a description of the invention as characterized in the claims, offering an improvement intended to overcome, at least in part, one of the aforementioned disadvantages of the known prior art.

According to a first aspect, the invention relates to a fluid connection device adapted and intended for connecting a first wall forming a first flexible pipe defining a first fluid space, to a second wall defining a second fluid space in the form of a second flexible pipe or flexible enclosure that is semi-rigid or rigid and disposable, in a biopharmaceutical assembly, comprising:

a first connector defining a first hollow passage, adapted and intended for connection to the first fluid space, a second connector, similar to the first connector, defining a second hollow passage, adapted and intended for connection to the second fluid space, the first connector and the second connector being adapted and intended to be coupled together in a genderless manner, by an insertion movement that is essentially an axial translation along the axis A, into a relative coupling position, which defines a mating plane P perpendicular to the main axis, each of the first and second connectors comprising, in an alternating manner along the circumferential direction, N flexible snap-fitting tabs and N stop surfaces, N being a strictly positive integer, the flexible snap-fitting tabs projecting axially forwards relative to the mating plane, and the stop surfaces being set back from the mating plane so that, in the coupling position, the snap-fitting tabs of one of the connectors clip into place beyond the stop surfaces of the other connector, such that the resulting position is locked by the snap-fitting tabs.

In this manner, a fluid connection device is proposed that is based on genderless connectors, which facilitates interoperability, modularity, and the formation of modular biopharmaceutical assemblies, because all the genderless connectors so formed can be connected to any another connector of the same genderless type, with no need to worry about the gender of each connector to be connected. In addition, there is no need to perform a rotational operation on the connection after the axial translational movement, which facilitates visual verification of the correct coupling position.

Advantageously, the snap-fitting tabs of one of the two connectors are formed integrally from the body of this connector, and each of the snap-fitting tabs move into the coupling position through a slot formed in a collar of the other connector. A collar is therefore provided which facilitates gripping and manually connecting the device, compatible with the compact arrangement of the clip-on means, in a genderless connector.

Advantageously, the snap-fitting tabs move apart outwardly during the coupling movement and return towards their rest position at the end of the coupling movement where they bear on the stop surfaces; in this manner the operator establishing the coupling has visual and/or auditory and/or haptic feedback on the proper coupling of the connectors.

Advantageously, each connector comprises a substantially cylindrical body, and in the coupling position the snap-fitting tabs lie adjacent to the body of the opposite connector and external thereto, and are resiliently biased radially inward if someone attempts to move them away from their rest position, such that they must all be moved apart simultaneously to unlock the connection. In this manner, the radial footprint of the locking device for this type of genderless connectors is quite optimized, and in addition the locking is particularly robust.

In one embodiment, each snap-fitting tab has a stirrup shape. This provides the snap-fitting tabs with satisfactory mechanical strength.

In one embodiment, the device may further comprise a protective cover formed by two half portions configured to close together in the radial direction to at least partially surround the first connector and the second connector, the cover serving as an indicator of proper coupling when snap-fitted into its closed position. In this manner, correct positioning of the protective cover is used to indicate proper coupling of the first and second connectors.

In one embodiment, the protective cover comprises two generally semi-cylindrical complementary portions connected by a flexible hinge portion, and the two portions are adapted to be snap-fitted together in an area diametrically opposite the hinge area, such that the protective cover is easily installed around the first and second connectors, in particular around their respective joined collars. Moreover, the protective cover may advantageously be molded as a single piece of synthetic material.

In one embodiment, the cover comprises an annular inner groove adapted to form, in the coupling position, a lock that immobilizes the adjacent collars that are respectively part of the first and second connectors. In this manner, the correct position of the protective cover reliably indicates that the first and second connectors are coupled and locked.

In one embodiment, the annular inner groove provides at least one tapered portion (having a trapezoidal cross-section) so as to exert axial pressure on the collars, which urges the two connectors closer together. The action of clipping the protective cover closed helps complete, if necessary, the movement of coupling the first and second connectors together.

In one embodiment, in the coupling position, the two connectors are arranged symmetrically relative to the mating plane, furthermore with an angular displacement of 360°/2N. This allows providing a simple genderless interface with several possible angular coupling positions, N possible angular positions in the current case.

In one embodiment, the number N is between 1 and 10, preferably equal to 4; whereby the number of possible angular positions for the coupling facilitates completion of the coupling.

In one embodiment, each connector further comprises a seal arranged radially inward within the cylindrical body, pressure being applied to the two seals in the axial direction when the two connectors are snap-fitted into position. This is a well-understood and standard solution for the sealing function of genderless connectors.

In one embodiment, each connector further comprises a temporary aseptic sealing membrane arranged on the front face of each of the seals, intended to be removed after coupling the connectors so that the two fluid spaces are placed in communication without any communication with the surrounding air; modular biopharmaceutical assemblies can thus be created under conditions of sterility or protection from the ambient air.

In one embodiment, the closing of the cover causes, after removal of the sealing membranes, additional travel in the coupling which increases the axial pressure between the seals; whereby the pressure on the seals is increased and the quality of the seal is improved.

In one embodiment, the connection device may further comprise a pipe clamp adapted and intended to be arranged around the end of the first pipe in order to clamp said pipe onto a tubular nozzle of the first connector, and the protective cover comprises at least one tubular extension adapted to be positioned, when the cover is clipped into the snap-fitted position, at least partially facing the pipe clamp in the radial direction, whereby the tubular extension prevents the pipe clamp from coming into direct contact with external elements. In this manner, the pipe clamp cannot come into direct contact with external elements, and this prevents possible damage to adjacent flexible bags or pipes by a damaging portion of the pipe clamp.

In one embodiment, the pipe clamp is a metal clamp having a general ring shape with at least one "ear", said ear being intended to be crimped to tighten the clamp, and the tubular extension is at a distance from the outer surface of the pipe. The crimped ear solution is a standard and well-understood solution for the pipe clamp function. In addition, several different diameters of flexible pipe and tubular nozzle are compatible with a single definition of the tubular extension of the protective cover.

In one embodiment, one of the connectors or the protective cover may further comprise an identifier such as a barcode or RFID tag or color code. In this manner, it is easy to access information concerning the flexible bag and/or the biopharmaceutical product contained therein, and traceability is facilitated.

In one embodiment, the snap-fitting tabs of the connectors each comprise a longitudinal extension which projects forward, so as to provide a gripping area for spreading apart the snap-fitting tabs in order to unlock the coupling position; this provides a solution for releasing the coupling of the first and second connectors.

In one embodiment, the device may further comprise a pipe clamp adapted and intended to be arranged around the end of the pipe in order to clamp said pipe onto a tubular nozzle of the first connector, and the snap-fitting tabs of the second connector each comprise a longitudinal extension which projects forward so as to cover, in the coupling position, the pipe clamp in the radial direction; whereby the extensions prevent the clamp from damaging nearby external elements, being without the addition of a cover as a separate part.

According to a second aspect, the invention relates to a genderless connector for fluid connection, adapted and intended for coupling to another similar genderless connector, in a fluid connection device as described above, the connector comprising, in an alternating manner along the circumference, N flexible snap-fitting tabs and N stop surfaces where N is a strictly positive integer, the flexible snap-fitting tabs projecting axially forward relative to the mating plane and the stop surfaces being set back from the mating plane such that, in the coupling position, the snap-fitting tabs of one of the genderless connectors clip onto the stop surfaces of the other similar genderless connector so that the resulting position is locked by the snap-fitting tabs, the mutual coupling being achieved in a substantially axial translational movement along axis A.

According to a third aspect, the invention relates to a biopharmaceutical assembly comprising a fluid connection device as described above.

According to a fourth aspect, the invention also concerns a method for forming a connection device as described above, the method comprising the steps of:

/a/ providing a first connector and a second connector, both with a compatible genderless interface, and each equipped with a collar and a seal with aseptic membrane closing off the opening defined by the seal, /b/ establishing a primary coupling of the first and second connectors, /c/ removing the aseptic sealing membranes, /d/ inserting a protective cover comprising an annular inner groove having a cross-section comprising two tapered shapes, the closing of the cover causing additional axial travel in the coupling to increase the contact pressure between the two seals.

In a fifth aspect, the invention also concerns a kit of parts comprising the first and second genderless connectors described above, optionally with a protective cover and optionally with at least one pipe clamp and a flexible pipe. In addition, the invention concerns the assembly of the above parts into an assembled state, optionally with the pipe clamp protected by the protective cover, or longitudinal extensions of the snap-fitting tabs.

BRIEF DESCRIPTION OF THE DRAWINGS

The figures of the drawings will now be briefly described.

FIG. 2 is an axial sectional view of the connection device of FIG. 1, in the coupled position, along section line II-II shown in FIG. 3.

FIG. 3 is a cross-sectional detailed view of the connection device of FIG. 1, in the coupled position, along section line shown in FIG. 2.

FIGS. 7A-7C represent an alternative embodiment, with temporary aseptic sealing membranes enabling the connection of connectors without exposure to the open air.

Figure 1:
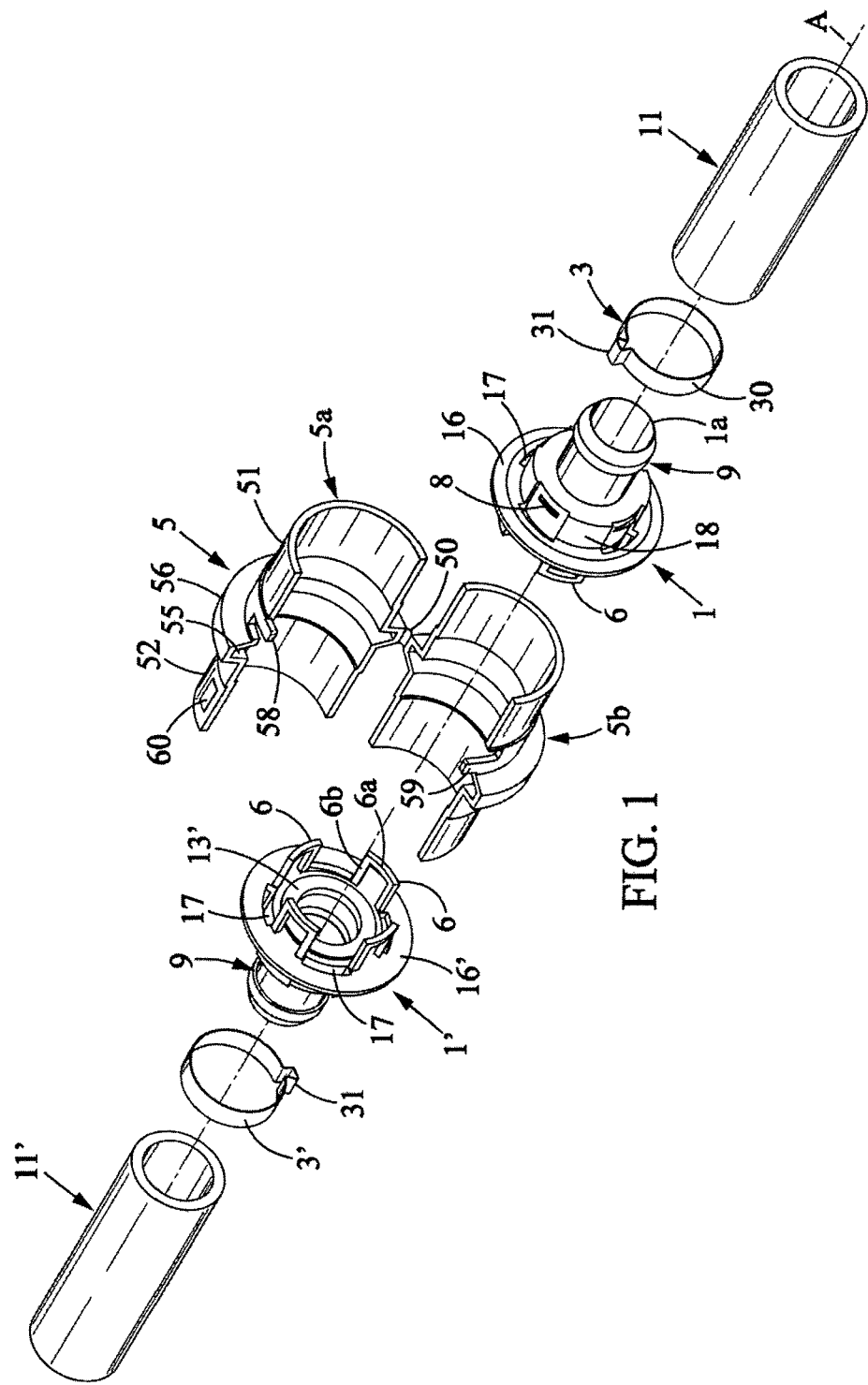
FIG. 1 is an exploded view of the connection device according to the invention.

Below is a detailed description of several embodiments of the invention, accompanied by examples and with reference to the drawings.

DETAILED DESCRIPTION OF THE INVENTION

In the example illustrated in FIGS. 1 to 4, a first flexible pipe 11 is connected to a second flexible pipe 11' in a biopharmaceutical assembly, by means of a fluid connection device 10 which comprises a first genderless connector 1 and a second genderless connector 1' which can be coupled.

The first flexible pipe 11 can be generally defined as a first wall 11 defining a first fluid space 71. Similarly, the second flexible pipe 11' can be generally defined as a second wall 11' defining a second fluid space 72.

The first connector 1 is made of synthetic material, more specifically it can be obtained by molding a plastic material, for example polypropylene, polyethylene, polycarbonate, polysulfone.

The first connector 1 comprises a tubular nozzle 9 at one end 1a, and a coupling interface with the second connector at the other end. The tubular nozzle 9 is symmetrical about the axis A. The coupling interface is a genderless interface that is intended to be inserted into an identical or similar interface that is also genderless. There is thus no male or female entity in such a genderless connection.

The first connector further comprises an intermediate portion which is in the form of a cylindrical body 18 centered on the axis A. A collar 16 extends radially outward from the cylindrical body 18. In this collar are formed a plurality of slots 17 evenly distributed around the circumference of the cylindrical body 18. In the illustrated example, there are four slots, each in the form of an arc of about 45°, these arcs allowing the passage of an element through the collar in an axial direction as will be seen below.

Inside the cylindrical body 18 there is a compressible seal 13; this seal is in the form of a ring centered on A and having a generally rectangular cross-section in the example illustrated. It comprises in particular a bearing face 13a intended to cooperate with another bearing face that is part of the seal of another opposing connector to which the first connector can be coupled. The seal 13 is preferably made of elastomeric material or silicone.

The front face 16a of the collar 16, in other words the face which is opposite the position of the tubular nozzle, and near or adjacent to a mating plane P, said mating plane defining a reference position for the mating of the bearing faces 13a of the seals of the two connectors in the coupled position.

Projecting beyond the mating plane, opposite the position of the tubular nozzle, are snap-fitting tabs 6 which in the illustrated example are in the form of a stirrup having a square cross-section. The snap-fitting tab has two longitudinal portions 6b extending from the collar, parallel to the axis A, and a transverse arcuate portion 6a connecting the ends of the two longitudinal portions 6b.

In the example illustrated, there are four snap-fitting tabs 6 which alternate with slots 17, previously described, and occupying the same diameter length as the slots 17 previously described, each snap-fitting tab defining an arc of approximately 45°.

Figure 4:
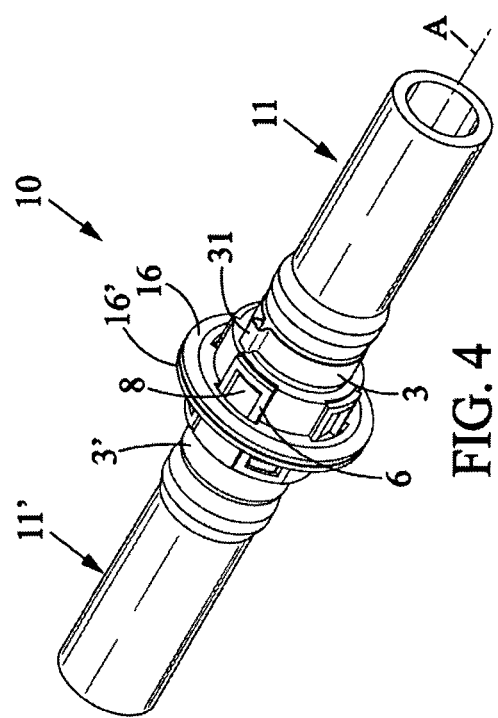
FIG. 4 is a perspective view of the connection device of FIG. 1 in the assembled position, shown without a protective cover.

Each snap-fitting tab 6 is intended to pass through the corresponding slot of the opposing connector, knowing that to couple a first connector to a second similar or identical connector 1', these must exhibit an angular offset so that the snap-fitting tab of the first is facing a slot of the second and vice versa (see FIGS. 1 and 4).

In addition, provided on the cylindrical body 18 of the connector, and set back relative to the mating plane and the collar, are stop surfaces 8 which may be provided as shoulders, said stop surfaces each being configured to cooperate with a transverse arm 6a of a snap-fitting tab, in the coupling position, thereby obtaining a clip-on effect, in other works locking the coupled position, as is apparent in FIG. 4.

One will note that the snap-fitting tabs 6 are adjacent to the cylindrical body 18 of the opposing connector 6; the snap-fitting tabs 6 are arranged outside the cylindrical body 18 of the opposing connector, and substantially mate with the outer contours of the cylindrical body.

Each stop surface 8 may be formed in a projection of the cylindrical body, comprising a slight anterior ramp to move apart the snap-fitting tabs during insertion of the connector and a posterior radial surface forming the stop surface 8 against which the transverse portion 6a of the snap-fitting tab comes to bear.

In FIG. 4, in the coupling position, the collars 16,16' are more or less adjacent to one another when the transverse portion 6a of the tabs abuts against the stop surfaces 8 under the reactive effect of the seal. It will be seen below that the space between the collars in the coupling position, which can be more or less significant, can be reduced to increase pressure between the seals.

Note that the snap-fitting tabs 6 are spread apart radially outward during the coupling movement so that each transverse portion 6a travels beyond the facing stop surface 8, which forms in the illustrated example a ramp for this purpose.

The second connector 1', to which the first connector can be coupled, is strictly identical to the first connector in form and material in the example illustrated in FIGS. 1 to 4. In particular, it comprises a tubular nozzle 9' to which the second flexible pipe 11' can be attached, a cylindrical body 18 with a collar 16', a seal 13', snap-fitting tabs 6, slots 17A, and stop surfaces 8, all of which are identical to those already described for the first connector.

However, the second connector may present more or less substantial differences provided that the coupling interface with the first connector remains compatible, in particular the position of the transverse arms of the snap-fitting tabs and the position of the stop surfaces, and to a lesser extent the passage provided by the slots.

In particular, the two connectors may be of different colors, which facilitates visual verification of proper coupling.

The tubular nozzle 9 comprises an annular bead 19, which in the illustrated example has a slight ramp 19a on the side of the flexible pipe 11 to be inserted and a shoulder 19b on the opposite side. The tubular nozzle may comprise a greater number of beads, for example successive catches as are known per se.

One will note that the inside diameter D1 of the tubular nozzle 9 is substantially similar to the inside diameter of the flexible pipe 11 at rest.

When the flexible pipe 11 is slid onto the tubular nozzle 9, the pipe is deformed radially outward by the shape of the ramp 19a, then as the insertion proceeds it returns to a narrower diameter 9a at the cylindrical bearing surface 9a.

The insertion can continue until the front end 11a of the pipe comes to bear against the rear part 18b of the cylindrical body 18 (see FIGS. 2 and 4).

Once the flexible pipe is inserted onto the tubular nozzle 9, a pipe clamp 3 is placed around the pipe at the abovementioned bearing surface 9a. It should be noted here that the pipe clamp 3 may be placed on standby around a rear portion of the pipe beforehand, prior to the insertion process. Once the clamp is in an appropriate position relative to the bearing surface of the tubular nozzle, the clamp is tightened.

The pipe clamp shown in the figures is a metal clamp with only one ear 31 provided for tightening. There could be more than one ear, however.

Pliers are used, for example, to flatten the ear shape 31 so as to reduce the diameter of the ring 30 formed by the pipe clamp 3. As a result, the pipe clamp then has a smaller diameter than that of the outer surface of the flexible pipe at rest, and therefore exerts a radial force directed inward.

This radial pressure has two objectives: the first is to ensure a sufficiently effective seal between the pipe 11 and the tubular nozzle 9, and the second is to mechanically retain the pipe around the nozzle to prevent the pipe from detaching from the tubular nozzle when pulled, due to the aforementioned shoulder 19b.

In addition, an optional protective cover 5 is advantageously provided which at least partially covers the first and second collars 16,16' that are part of the first and second connectors 1,1' respectively, as is apparent in FIG. 2.

The protective cover 5 is formed by two parts 5a, 5b forming two half-portions of similar size joined by a flexible hinge portion 50, all obtained in a single molding operation. Specifically, each part may be in the form of a semi-cylindrical portion with a protruding ring 56 in the central area, although other shapes are possible. The two portions are intended to be clipped together in an area diametrically opposite the hinge area, for example by means of hooks 58,59 that clip together, which are simply and symbolically represented in FIG. 1.

Once the protective cover is installed around the collars of the first and second connectors 1,1', the cover 5 thus forms an indicator of proper coupling of the connectors: if the collars 16,16' are too far apart, the protective cover cannot be closed around them.

Advantageously, the cover comprises an annular inner groove 55 adapted to form, in the coupling position, a lock that immobilizes the adjacent collars 16,16' against one another as is apparent in FIG. 2.

In addition, the inner groove may comprise at least one tapering portion 53,54 (of trapezoidal cross-section) so as to exert axial pressure on the collars, which urges the two connectors closer together and increases the mutual contact pressure between the seals 13,13'.

In addition, to facilitate the movement of closing the two half-portions of the cover on the collars, the radially external rear portion of the collars 16b may comprise a chamfer 16b which facilitates sliding along the tapering portions 53,54.

In addition, the protective cover 5 may be such that it forms protective elements for the first pipe clamp 3 on the first connector 1 and/or for the pipe clamp 3' of the second connector 1'.

More specifically, the protective cover comprises a first axial extension 51 in the first connector direction and a second axial extension 52 in the second connector direction. In the example shown, the protective cover is thus symmetrical relative to the mating plane P of the coupling. Its installation can therefore be oriented in one direction or the opposite direction.

The first axial extension 51 forms such "protective elements" for the first pipe clamp 3: in effect the pipe clamp, in the coupling position, is positioned within the inner region defined by this axial extension 51. In this manner, if during handling or movement of the connection device, the device comes into contact with external elements 90, then it is not the pipe clamp which will be in contact with said external elements 90 but instead it will be the protective cover 5, here the axial extension 51, which will come into contact with the external element(s) 90 (see FIG. 2). Thus, damage from contact with a potentially damaging portion of the clamp 3 can be advantageously avoided.

The same arrangements and advantages are obtained, mutatis mutandis, for the second connector and its pipe clamp 3".

It should be noted that the axial extensions may have different shapes: they may be a plurality of separate tabs distributed around the circumference, or a plurality of separate cylindrical wall portions distributed around the circumference.

Note that the first connector 1 defines a first hollow passage intended to be placed in fluid communication with the first space 71. Similarly, the second connector defines a second hollow passage intended to be placed in fluid communication with the second space 72 (the inside of the second pipe in the example shown).

Figure 5:
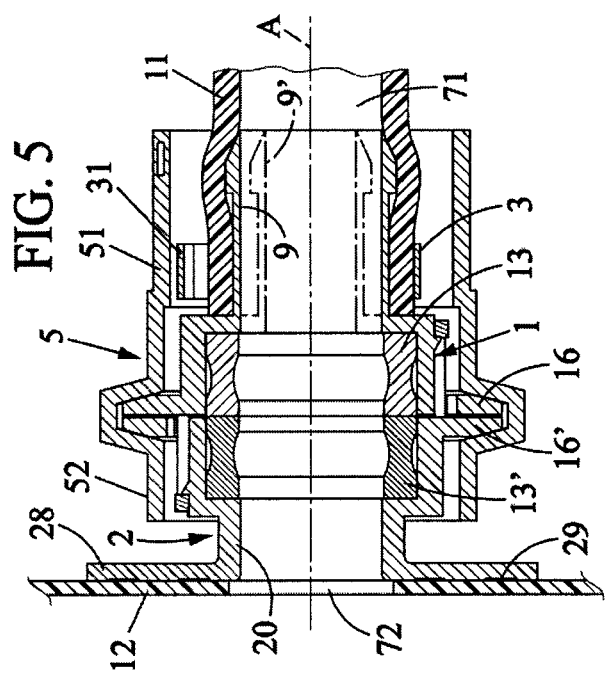
FIG. 5 represents another embodiment, in an axial sectional view, where the second connector comprises a base fixed to a biopharmaceutical enclosure.

In another embodiment shown in FIG. 5, the second connector 2 is not intended to receive a flexible pipe, but rather to be secured to a container 12 intended to hold biopharmaceutical fluid. The container can be generally defined as a flexible enclosure 12 formed by a second wall defining a second fluid space 72.

A wide disc 28 equipped with a central hole is fixed by welding 29 to the wall 12 of the flexible enclosure. A tubular portion 20 extends from the wide disc 28 to the cylindrical body 18 comprising the stop surfaces 8, collar 16', and seal 13'.

In this embodiment, there is no second pipe clamp, and furthermore the axial length of the second connector 2 is shorter than the axial length of the first connector 1. As a result, the protective cover 5 suitable for this application is asymmetrical relative to the mating plane P, the second tubular extension 52 being shorter than the first tubular extension 51. However, the shape of the annular inner groove 55 is quite similar to what has been described above, as are the protection means for the pipe clamp 3.

Note that FIG. 5 illustrates that it is possible to provide several different diameters of nozzles 9,9' for one genderless coupling interface, which facilitates modularity and the creation of biopharmaceutical assemblies using various pipe diameters.

Figure 6:
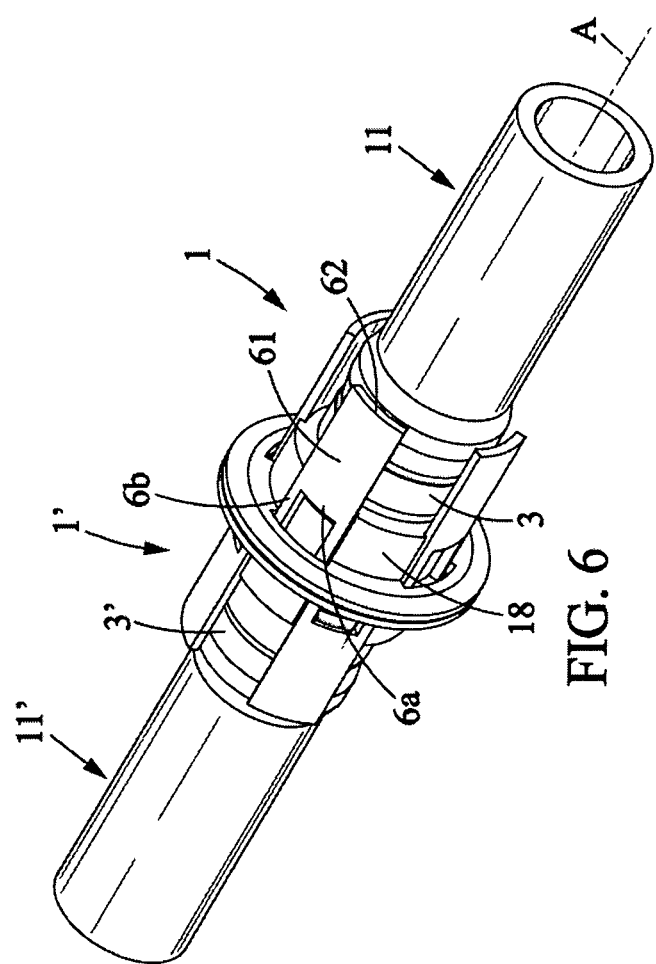
FIG. 6 illustrates an alternative embodiment wherein the snap-fitting tabs comprise an axial extension of extra length.

In a variant shown in FIG. 6, the snap-fitting tabs 6 each comprise an axial extension 61 which extends the tab frontward, thereby forming an extra length projecting beyond the body of the opposing connector in the coupling position. All other characteristics are similar or identical to what has been described above. There is not necessarily a protective cover in this mode.

In the illustrated example, the axial longitudinal extension 61 of the snap-fitting tabs of the second connector 1' extends significantly beyond the body 18 of the first connector, and therefore the end 62 of this extension is at a distance from the pipe, allowing the operator to manipulate the tab or tabs with his fingers.

In addition, these frontward axial extensions form protective elements for the pipe clamp 3 of the first connector, preventing a damaging edge of the clamp from coming into direct contact with an external element 90.

As is apparent from FIG. 6, in a symmetrical manner, the first connector 1 also comprises axial longitudinal extensions of the snap-fitting tabs so as to protect the second pipe clamp 3'. However, symmetry is not required because the axial extensions of the tabs are not directly implicated in the coupling compatibility of the genderless connectors.

In a variant shown in FIG. 7A, each of the first and second connectors is equipped with an aseptic sealing membrane prior to its coupling. A first membrane 73 is arranged on the front face of seal 13, and similarly a second membrane 74 is arranged on the front face of seal 13' of the second connector.

Note that in this embodiment, each of the connectors comprises only two snap-fitting tabs in order to leave enough room for installation and removal of the aseptic sealing membrane.

A primary clip-on position is defined, which can be considered an intermediate position in the present embodiment. In this primary clip-on position, the transverse portion 6a of the snap-fitting tabs 6 is placed in abutment against the stop surfaces 8, but the collars 16,16' are not in contact with one another and are separated by a free space, each collar being, in this position, set slightly back from the interface plane P.

All other elements not described again here are assumed to be identical or similar to what was presented for the first embodiment.

In the initial connecting stage, the connectors 1,1' are apart from each other and the fluid spaces 71,72 are isolated from each other and from the ambient air.

To perform the connection, first a primary coupling is made between the first and second connectors 1,1', as described above, in a maneuver similar to that described for the first embodiment. FIG. 7B illustrates this primary coupling position where the aseptic membranes are sandwiched between the seals 13,13' of the two connectors, which are exerting a certain axial pressure against one another.

Next, the aseptic sealing membranes 73,74 are removed by pulling them radially as illustrated by arrow R of FIG. 7B.

The two fluid spaces 71,72 have now been placed in communication without having been in contact with the ambient air.

For some applications, this represents a sufficient solution for a connection satisfying conditions of isolation and sterility with respect to ambient air.

Advantageously, when using a protective cover 5 such as the one presented above and as illustrated in FIG. 7C, the movement of closing the cover is utilized to exert an axial pressure. As the tapered shapes of the annular inner groove have a trapezoidal cross-section, closing the cover causes additional axial travel in the coupling to bring the collars 16,16' closer together and thus increase the contact pressure between the two seals.

When a protective cover is used in this manner, the axial pressure of the primary coupling may be substantially reduced to facilitate removal of the aseptic sealing membranes.

In addition, an optional feature is provided that is compatible with all variants mentioned above: this is the integration of at least one identifier 60, such as a barcode or electronic tag (for example RFID). Preferably, this identifier is provided on the first connector, and/or on the second connector, and/or on the protective cover as illustrated in FIG. 1. The identifier could also be a colored dot or a color coding of the part itself.

Note that according to the invention, the number N of snap-fitting tabs may be any positive integer from 1 to ten.

The invention claimed is:

1. A fluid connection device adapted and intended for connecting a first wall forming a first flexible pipe defining a first fluid space, to a second wall defining a second fluid space in the form of a second flexible pipe or flexible enclosure that is semi-rigid or rigid and disposable, in a biopharmaceutical assembly, comprising:
   a first connector defining a first hollow passage, adapted and intended for connection to the first fluid space,
   a second connector defining a second hollow passage, adapted and intended for connection to the second fluid space,
   the first connector and the second connector being adapted and intended to be coupled, by an insertion movement that is an axial translation along the axis (A), into a relative coupling position, which defines a mating plane perpendicular to the main axis,
   each of the first and second connectors comprising, in an alternating manner along the circumferential direction, N flexible snap-fitting tabs and N stop surfaces, N being a strictly positive integer,
   the flexible snap-fitting tabs projecting axially forwards relative to the mating plane, and the stop surfaces being set back from the mating plane so that, in the coupling position, the snap-fitting tabs of one of the connectors clip into place beyond the stop surfaces of the other of the connectors, such that the resulting position is locked by the snap-fitting tabs,
   wherein the snap-fitting tabs of one connector are formed integrally from the body of the connector, and each of the snap-fitting tabs moves into the coupling position through a slot formed in a collar of the other connector, wherein each connector comprises a cylindrical body and wherein in the coupling position the snap-fitting tabs lie adjacent to the cylindrical body of the opposing connector and externally thereto, the snap-fitting tabs moving apart outwardly during the coupling movement and being resiliently biased radially inward when there is attempted movement of them away from their rest position, such that they must all be moved apart simultaneously in order to unlock the connection, so that the position thus obtained is locked by the snap-fitting tabs,
   a protective cover formed by two half-portions configured to close together in the radial direction to at least partially surround the first connector and the second connector, the protective cover serving as indicator of proper coupling when snap-fitted into its closed position, and wherein a pipe clamp adapted and intended to be arranged around the end of the pipe in order to clamp said pipe onto a tubular nozzle of the first connector, and wherein the protective cover comprises at least one tubular extension adapted to be positioned, when the protective cover is clipped into the coupling position the pipe clamp is surrounded by the protective cover, whereby the tubular extension prevents the pipe clamp from coming into direct contact with external elements.

2. The device according to claim 1, wherein each snap-fitting tab has a stirrup shape.

3. The device according to claim 1, wherein the two half-portions are generally complementary and semi-cylindrical, connected by a flexible hinge portion, the two portions being adapted to be snap-fitted together in an area diametrically opposite the hinge area.

4. The device according to claim 1, wherein the protective cover comprises an annular inner groove adapted to form, in the coupling position, a lock that immobilizes the adjacent collars that are respectively part of the first and second connectors.

5. The device according to claim 1, wherein the annular inner groove provides at least one tapered portion so as to exert axial pressure on the collars, which urges the two connectors closer together.

6. The device according to claim 1, wherein, in the coupling position, the two connectors are arranged symmetrically relative to the mating plane, furthermore with an angular displacement of 360°/2N.

7. The device according to claim 1, wherein each connector further comprises a seal arranged radially inward within the cylindrical body, pressure being applied to the two seals in the axial direction when the two connectors are snap-fitted into position.

8. The device according to claim 7, further comprising a temporary aseptic sealing membrane arranged on the front face of each of the seals, and intended to be removed after coupling the connectors so that the two fluid spaces are placed in communication without any communication with the surrounding air.

9. The device according to claim 8, wherein the closing of the protective cover causes, after removal of the sealing membranes, additional travel in the coupling which increases the axial pressure between the seals.

10. The device according to claim 1, wherein one of the connectors or the protective cover further comprises an identifier such as a barcode or RFID tag or color code.

11. The device according to claim 1, wherein the snap-fitting tabs of the connectors each comprise a longitudinal extension which projects forward, so as to provide a gripping area for spreading apart the snap-fitting tabs in order to unlock the coupling position.

12. The device according to claim 1, further comprising a pipe clamp adapted and intended to be arranged around the end of the pipe in order to clamp said pipe on a tubular nozzle of the first connector, and wherein the snap-fitting tabs of the second connector each comprise a longitudinal extension which projects forward so as to cover, in the coupling position, the pipe clamp in the radial direction.

13. A biopharmaceutical assembly comprising a fluid connection device according to claim 1.

\* \* \* \* \*